United States Patent
Riley et al.

(10) Patent No.: US 7,803,977 B2
(45) Date of Patent: Sep. 28, 2010

(54) TRANSALKYLATION OF HEAVY ALKYLATE USING A LAYERED CATALYST

(75) Inventors: Mark G. Riley, Des Plaines, IL (US); Deng-Yang Jan, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 573 days.

(21) Appl. No.: 11/687,012

(22) Filed: Mar. 16, 2007

(65) Prior Publication Data

US 2008/0228018 A1  Sep. 18, 2008

(51) Int. Cl.
*C07C 6/12* (2006.01)
(52) U.S. Cl. ........................................ 585/475
(58) Field of Classification Search ................ 585/475
See application file for complete search history.

(56) References Cited

U.S. PATENT DOCUMENTS

| 4,051,191 A | 9/1977 | Ward ........................ 260/671 R |
| 4,857,666 A | 8/1989 | Barger et al. ................. 585/323 |
| 5,434,326 A | 7/1995 | Gajda et al. .................. 585/467 |
| 6,376,730 B1 | 4/2002 | Jan et al. ..................... 585/467 |
| 2002/0082460 A1* | 6/2002 | Verduijn et al. ............. 585/475 |

* cited by examiner

*Primary Examiner*—Thuan Dinh Dang
(74) *Attorney, Agent, or Firm*—Arthur E. Gooding

(57) ABSTRACT

A layered catalyst is disclosed for use in transalkylation of polyalkylated benzenes. The catalyst comprises an inner core material with a molecular sieve bonded over the core. The process minimizes the cracking of the alkyl groups during the transalkylation reaction.

8 Claims, No Drawings

TRANSALKYLATION OF HEAVY ALKYLATE USING A LAYERED CATALYST

FIELD OF THE INVENTION

This invention relates to an improved molecular sieve and its use for the conversion of hydrocarbons. More specifically, the invention concerns the use of a specialized molecular sieve for the transalkylation of heavy alkylates.

BACKGROUND OF THE INVENTION

The alkylation of aromatic hydrocarbons such as benzene is a well-developed art, and one that is practiced commercially using solid catalysts in large scale industrial units. Two common commercial applications are the production of ethyl benzene and cumene (isopropyl benzene). The production of ethyl benzene is the process of alkylating benzene with ethylene to produce ethyl benzene, which is the precursor used in the production of styrene. The production of cumene is the process of alkylating benzene with propylene to form isopropylbenzene, and which is used in the production of phenol. The production of ethyl benzene and cumene have undergone continual improvement, and an example of the process and typical flow scheme is shown in U.S. Pat. No. 4,051,191.

In the trans-alkylation of poly-ethylbenzene or poly-isopropylbenzene with an aromatic substrate, the issues of isomerization either do not exist or take place to a very minimal degree. Furthermore, the cyclization or cracking of the alkyl groups do not take place due to the lack of favorable mechanistic pathways. However, the situation is quite different in the trans-alkylation of poly-alkylated benzene, where the alkyl groups have 5 or more carbon atoms. Here the alkyl groups will undergo isomerization, followed by cyclization or cracking reactions. Cyclization of the alkyl groups results in multiple ring compounds, potentially accelerating the catalyst deactivation. The cracking of alkyl groups leads to light hydrocarbon products, potentially leading to lower yields and complicated separation situations. Due to the nature of consecutive reactions of cyclization and cracking processes, it would be beneficial to have the active sites confined to an outer layer to limit the diffusion path of the reactant and primary product, the linear alkylbenzene (LAB).

Therefore, improvements in the catalyst structure can make for more efficient processing while reducing the expense of the catalyst.

BRIEF SUMMARY OF THE INVENTION

The invention is a process for the transalkylation of a polyalkyl aromatic compound where the alkyl groups on the aromatic compound have six or more carbon atoms. The process comprises passing an aromatic hydrocarbon substrate and a polyalkylated aromatic hydrocarbon substrate to a reaction zone. The aromatic hydrocarbon and the polyalkylated aromatic hydrocarbon are reacted over a solid catalyst comprising a layered structure, thereby generating an effluent stream comprising a monoalkylated aromatic hydrocarbon.

In one embodiment, the process is carried out under reaction conditions that include a pressure between 100 kPa and 13 MPa, a temperature between 40° C. and 400° C., and a liquid hourly space velocity between 0.1 and 50 $hr^{-1}$. The process is carried out at conditions to preferably maintain the reactants in a liquid phase.

In another embodiment, the process is carried out with the layered catalyst having an inert core with an effective diameter between 0.05 mm and 5 mm, with the catalyst in a layer over the inert core with a thickness between 10 micrometers to 300 micrometers. The inert core is selected, but not limited to, from materials such as inorganic oxides, clays, nitrides, carbides, borosilicates, silicas, and mixtures thereof. The catalyst is selected, but not limited to, from amorphous silica-alumina, acidic clays, pillared clays, mesoporous crystalline materials, solid phosphoric acid, $AlCl_3$, alumino-phosphates, heteropolyacids, UZM-5, UZM-8, MCM-22, MCM-49, MCM-56, large pore molecular sieves, and mixtures thereof.

Other objects, advantages and applications of the present invention will become apparent to those skilled in the art from the following detailed description and drawings.

DETAILED DESCRIPTION OF THE INVENTION

The process of alkylating benzene for the production of alkyl benzenes generates monoalkylated benzenes and polyalkylated benzenes. Polyalkylated benzenes are also known as heavy alkylates. Monoalkylated benzenes, and especially linear alkylbenzenes are useful in a many utilities, the most prominent of which is the use to make detergents and similar products by sulfonating the alkylbenzenes to make alkylbenzene sulfonates. The performance of these products is affected by the nature of the alkylbenzene, and especially when there are multiple alkyl groups on the benzene.

Monoalkylbenzenes are much more useful and work much better in detergents than polyalkylbenzenes (PABs) and therefore conversion of polyalkylbenzenes to monoalkylbenzenes is very desirable. The main problem with conversion of polyalkylbenzenes is the cracking of the alkyl groups attached to the benzene rings. Another difficulty is in the maintenance of linear alkylbenzenes (LABs). It is easy to make branched alkylbenzenes because the alkyl groups are readily isomerized. This is very undesirable as branched alkylbenzenes (BABs) are very difficult to biodegrade in the environment, and therefore disfavored. With smaller alkyl groups, such as ethyl and propyl groups one can use a zeolite when there is a relatively low benzene to polyalkylate ratio. However, in the detergent application the alkyl groups are larger and one must select catalysts with good transport properties, i.e. good diffusion characteristics, due to the larger molecules.

Transalkylation for polyalkylbenzenes where the alkyl groups are large, or greater than 5 carbon atoms, has similar chemistry to the transalkylation with ethylbenzene and cumene, except that the longer chain alkyl groups can isomerize, whereas the ethyl and propyl groups cannot. If practiced poorly, it is easy to make branched alkylbenzene instead of linear alkylbenzene, which is the production of poor quality material and very expensive in the long run. Another difference is the choice of catalyst, as well as the associated operating conditions. The present invention provides for converting polyalkylbenzenes to monoalkylbenzenes while maintaining linearity of the alkyl groups. The polyalkylbenzenes are primarily dialkylbenzenes. The maintenance is important for product quality. If there is to much isomerization and the linearity is significantly reduced during the transalkylation process, the process becomes undesirable.

The present invention is a process for aromatic trans-alkylation comprising passing a first stream comprising an aromatic substrate hydrocarbon and a second stream comprising an aromatic hydrocarbon having more than one alkyl group to a reaction zone, where each alkyl group has 6 or more carbon atoms. The aromatic hydrocarbon in the first stream is reacted with the polyalkyl aromatic hydrocarbon in the second stream over a solid catalyst comprising a layered structure, thereby generating an effluent stream comprising a monoalkylated aromatic hydrocarbon. A polyalkyl aromatic hydrocarbon is an aromatic hydrocarbon that has been alkylated with two or more alkyl groups. The preferred product is for a monoalkylated aromatic hydrocarbon with an alkyl group having from 8 to 16 carbon atoms, and therefore the reactants are preferred to have alkyl groups each having a size from 8 to 16 carbon atoms.

The reaction is carried out at a pressure between 100 kPa and 13 MPa, and preferably between 1 MPa and 4 MPa. The reaction is further carried out at a temperature between 40° C. and 400° C., with a preferred operating temperature between 100° C. and 250° C. The temperature and pressure are adjusted to maintain the process such that the first stream and second stream when mixed in the reaction zone are in a liquid phase. The liquid flows in the reactor are maintained to obtain a liquid hourly space velocity of between 0.1 and 50 $hr^{-1}$, and preferably between 0.5 and 5 $hr^{-1}$.

The choice of catalyst along with the process parameters for maintaining optimal contact times for the reaction is just as important. An important aspect for controlling contact time is through having a catalyst with a relatively large surface area, yet limiting the amount of time the reactants are in contact with the catalyst. This includes producing a catalyst pellet where the reactants cannot migrate far into the catalyst pellet. To that extent, the catalyst pellet is preferably a layered catalyst pellet, where it comprises an inert inner core with a relatively thin layer of catalyst material surrounding the inner core. The size of catalyst pellet, or particles, can have a characteristic size in range from 0.05 mm to greater than 5 mm, though the usual commercial production produces catalyst particle sizes in a narrower size range. The characteristic size refers to a length dimension that is equivalent to a sphere having a diameter equal to the characteristic size. The catalyst particle has a thin layer of catalytic material laid over the inert core, where the layer has a thickness between 10 micrometers to 300 micrometers.

The inner core of the catalyst particles comprises an inert material that can withstand harsh operating conditions. Materials useable in the inner core include, but are not limited to, inorganic oxides such as cordierite, mullite, olivine, zirconia, spinel, kyanite, aluminas, silicas, aluminates, silicates, titania, nitrides, carbides, borosilicates, boria, aluminum silicates, magnesia, fosterite, kaolin, kaolinite, montmorillonite, saponite, bentonite, and mixtures thereof. The inner core is preferably impermeable, or made of a material with a very low permeability. Optionally, the inner core is a low permeability structure, including a structure having a porous inner subcore and an impermeable outer sublayer on the inner core. The use of low permeability materials for the inner core allows for the use of clays that have little or low acidic activity, and thus having limited access to potential acidic sites and having an insignificant contribution to overall reactions. Additional materials available for use in the inner core include gamma alumina, delta alumina, eta alumina, and theta alumina, which are inert or have very low acidic activity.

These materials which form the inner core can be formed into a variety of shapes such as pellets, extrudates, spheres or irregularly shaped particles although not all materials can be formed into each shape. Preparation of the inner core can be done by means known in the art such as oil dropping, pressure molding, metal forming, pelletizing, granulation, extrusion, rolling methods and marumerizing. A spherical inner core is preferred. The inner core whether spherical or not has an effective diameter of about 0.05 mm to about 5 mm and preferably from about 0.2 mm to about 4 mm. For a non-spherical inner core, effective diameter is defined as the diameter the shaped article would have if it were molded into a sphere. Once the inner core is prepared, it is calcined at a temperature of about 400° C. to about 1500° C.

The catalyst material in the catalyst particles are solid catalysts having moderate to high acidity. The catalysts also can have large pores for the molecules and to limit the residence time an alkylbenzene is in contact with the catalyst. These materials include, but are not limited to, amorphous silica-alumina, acidic clays, pillared clays, mesoporous crystalline materials such as MCM-41, solid phosphoric acid, $AlCl_3$, alumino-phosphates, heteropolyacids, UZM-5, UZM-8, MCM-22, MCM-49, MCM-56, large pore molecular sieves, and mixtures of thereof. In one embodiment, the catalyst material comprises acidic clays which include, but are not limited to, montmorillonite, beidellite, hectonite, saponite, and mixtures thereof.

In another embodiment, the catalyst material comprises a heteropolyacid. A heteropolyacid is a chemical compound composed of a transition metal, oxygen, an element from the p-block of the periodic table, such as silicon, phosphorus, sulfur or arsenic, and acidic hydrogen atoms. The heteropolyacids for use in the present invention comprise cation-exchanged heteropolyacids.

In another embodiment, the catalyst material comprises a sulfate metal oxide of a Group IV transition metal element, a sulfate rare earth-stabilized metal oxide of a Group IV transition metal element, or a mixed metal oxide or rare earth-stabilized mixed metal oxide made up of Group IV and Group VI transition metal elements. Group VI metals include titanium (Ti), zirconium (Zr), and hafnium (Hf). Group VI metals include chromium (Cr), molybdenum (Mo), and tungsten (W). Rare earth metals are the metals in the actinide series and the lanthanide series of the periodic table.

In yet another embodiment the catalyst material comprises a large pore molecular sieve, which include, but are not limited to, FAU materials, BEA materials, MOR materials, LTL materials, BPH materials, MTW materials, MEI materials, MWW materials, and mixtures thereof. Large pore molecular sieves comprise molecular sieves having pores comprising 12 membered rings or larger.

Transalkylation involves separating a polyalkylated aromatic from a product stream comprising mono- and polyalkylated aromatics. The polyalkylated aromatic compound is directed to a transalkylation reactor with the aromatic substrate hydrocarbon, which in one embodiment is benzene. The polyalkylated aromatic and benzene are contacted with a transalkylation catalyst to react and form a monoalkylated aromatic compound. Usually an excess of the benzene is used to promote only the formation of monoalkylates. The challenge in the trans-alkylation of PAB's where the alkyl groups have 5 or more carbon atoms is that the alkyl groups will undergo isomerization, followed by cyclization of cracking reactions. Cyclization of the alkyl groups results in multiple ring compounds, potentially accelerating the catalyst deactivation. The cracking of alkyl groups leads to light hydrocarbon products, potentially leading to lower yields and a complicated separation situation. Due to the nature of consecutive reactions in cyclization and cracking processes, it would be beneficial to have the active sites confined to an outer layer to limit the diffusion path of the reactant and primary product, the linear alkyl benzene (LAB).

While the invention has been described with what are presently considered the preferred embodiments, it is to be understood that the invention is not limited to the disclosed embodiments, but it is intended to cover various modifications of the plates, combinations of plates, and equivalent arrangements included within the scope of the appended claims.

The invention claimed is:

1. An aromatic transalkylation process comprising:

passing a first stream comprising an aromatic substrate hydrocarbon and a second stream comprising an polyalkyl aromatic hydrocarbon having more than one alkyl group to a reaction zone, wherein each alkyl group has 6 or more carbon atoms;

reacting the aromatic substrate hydrocarbon in the first stream with the polyalkyl aromatic hydrocarbon in the second stream over a solid catalyst consisting of an inert core consisting of a solid material selected from the group consisting of cordierite, mullite, olivine, zirconia, spinel, kyanite, aluminas, silicas, aluminates, silicates, titania, nitrides, carbides, borosilicates, boria, aluminum silicates, magnesia, fosterite, kaolin, kaolinite, montmorillonite, saponite, bentonite, clays that have little or low acidic activity, gamma alumina, delta alumina, eta alumina, theta alumina and mixtures thereof, the core having an effective particle diameter between 0.05 mm and 5 mm, with an outer layer having a thickness between 10 and 300 micrometers of catalytically active material selected from the group consisting of UZM-5, UZM-8, MCM-22, MCM-49, MCM-56, and mixtures thereof bound to the inert core, thereby generating an effluent stream comprising a monoalkylated aromatic hydrocarbon.

2. The process of claim 1 wherein each alkyl group has from 8 to 16 carbon atoms.

3. The process of claim 1 wherein the reacting conditions include a pressure between 100 kPa and 13 MPa.

4. The process of claim 3 wherein the reacting conditions include a pressure between 1 MPa and 4 MPa.

5. The process of claim 1 wherein the reacting conditions include a temperature between 40° C. and 400° C.

6. The process of claim 5 wherein the reacting conditions include a temperature between 100° C. and 250° C.

7. The process of claim 1 wherein the reacting conditions include a liquid hourly space velocity between 0.1 and 50 $hr^{-1}$.

8. The process of claim 7 wherein the reacting conditions include a liquid hourly space velocity between 0.5 and 5 $hr^{-1}$.

* * * * *